United States Patent [19]

Taskis

[11] 4,423,033

[45] Dec. 27, 1983

[54] PHARMACEUTICAL COMPOSITIONS

[75] Inventor: Charles B. Taskis, Worthing, England

[73] Assignee: Beecham Group Limited, England

[21] Appl. No.: 230,312

[22] Filed: Feb. 2, 1981

Related U.S. Application Data

[63] Continuation of Ser. No. 73,100, Sep. 6, 1979, abandoned.

[30] Foreign Application Priority Data

Dec. 8, 1978 [GB] United Kingdom ............... 47768/78

[51] Int. Cl.$^3$ ...................... A61K 31/79; A61K 31/43

[52] U.S. Cl. ....................................... 424/80; 424/271
[58] Field of Search ................................... 424/80, 271

[56] References Cited

FOREIGN PATENT DOCUMENTS 1532993 11/1978 United Kingdom ............... 424/271

Primary Examiner—Jerome D. Goldberg
Attorney, Agent, or Firm—Jacobs & Jacobs

[57] ABSTRACT

An injectable formulation containing a soluble salt of amoxycillin has its stability on reconstitution improved by the incorporation therein of PVP.

11 Claims, No Drawings

PHARMACEUTICAL COMPOSITIONS

CROSS REFERENCE

This is a continuation of Ser. No. 073,100 filed Sept. 6, 1979 now abandoned.

This invention relates to pharmaceutical compositions. More specifically this invention relates to a pharmaceutical composition containing amoxycillin which may be administered by injection.

British Pat. No. 1,241,844 discloses inter alia amoxycillin and its salts. Amoxycillin, which is the penicillin of the formula:

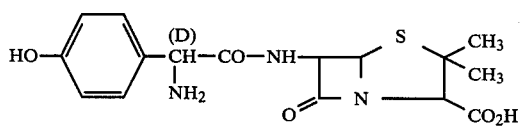

is widely recognised as having a broad spectrum of anti-bacterial activity of a high order. One of amoxycillin's great advantages is that it is very well absorbed after oral administration but there are occasions when it is desirable to administer it parenterally.

It has now been found that the use of a certain additive with soluble salts of amoxycillin provides a pharmaceutical composition which on reconstitution for injection has particularly good stability.

Accordingly the present invention provides a pharmaceutical composition, which on reconstitution with water yields an injectable solution, which composition comprises a water soluble salt of amoxycillin, and polyvinylpyrrolidone of molecular weight 1000 to 12000.

The polyvinylpyrrolidone (hereinafter referred to as PVP) used in the composition of this invention has a molecular weight of from 1000 to 12000. Since the material is a polymer it will be realised by a chemist that the molecular weight referred to is an average molecular weight. A suitable method of determining the average molecular weight of PVP for use in this composition is gel permeation chromatography. The PVP should not contain molecules with molecular weight of more than 30000; similarly it should not have a monomer content of more than 1%. The K value of suitable PVP will generally be between 10 and 18.

Favourably the PVP employed will have a molecular weight of 1500 to 6000.

A preferred PVP for use in the composition will have a molecular weight of 2000 to 3500. A PVP of this kind is Kollidon CE 5080 (Kollidon is a Registered Trade Mark) which is available from BASF Aktiengesellschaft, D-6700 Ludwigshafen, Federal Republic of Germany. This PVP has a K value of 12 to 14, which is a favoured range.

Normally the weight ratio of the amoxycillin salt (taken as the free acid equivalent weight) to PVP in the compositions of the invention will be 1:0.25 to 1:5, more suitably 1:0.5 to 1:3.

Suitably the amoxycillin salt is the sodium or potassium salt and preferably it is the sodium salt.

It has been found that the compositions of this invention can also usefully contain a water soluble solid acidic material. Suitable examples of such materials include organic acids such as citric, tartaric, malic, ascorbic, gluconic, maleic, succinic and aconitic acids. Preferably such acids will not contain a hydroxy group. It is presently believed that maleic acid is one of the most preferred organic acids to include in the compositions of the invention. Suitable acidic materials also include inorganic materials such as sodium dihydrogen phosphate.

When the aforesaid acidic materials are present in the compositions, then suitably the weight ratio of amoxycillin to the material is in the range 100:1 to 10:1, more suitably 75:1 to 25:1.

Generally we have found that, when an acidic material is present, higher proportions of the acid can be used when higher proportions of PVP are present.

The compositions of this invention may be reconstituted with an aqueous solvent, for example water, in conventional manner, the ingredients either being dissolved simultaneously or consecutively.

The compositions of this invention will normally be presented in a glass vial. Such vials may be filled in conventional manner with the amoxycillin salt and PVP in powder form. Alternatively of course the amoxycillin salt and the PVP can be presented in separate containers in a twin pack, for example each in a separate glass vial. In such cases the PVP may be in aqueous solution, so that the composition may simply be reconstituted by mixing together the contents of the two containers.

It will be appreciated that as the compositions of the invention are to be used only after reconstitution into a solution, then the exact physical form of the amoxycillin salt and the PVP in the (dry) compositions is unimportant. Thus while conveniently the amoxycillin salt and the PVP may merely be in a powder admixture, we have found that the product of the process described in our co-pending patent application (Ser. No. 073,101) of even date entitled "A process for the preparation of sodium amoxycillin" claiming priority from U.K. patent application No. 47744/78, filed Dec. 8, 1978 (the disclosure of which is hereby incorporated by reference), may also be used. This product is a solid solution of a water soluble salt of amoxycillin in the PVP, and forms an important aspect of this invention. Suitable and preferred PVPs, and ratios of amoxycillin salt to PVP, in this product are as herein described.

The following Examples illustrate this invention.

EXAMPLE 1

The following composition was prepared by dry mixing the following ingredients:
Sodium amoxycillin: 250 mg. p.f.a.
PVP (Kollidon 12 PF): 300 mg
This composition was reconstituted in water (1.5 ml). The resulting solution showed a 10% potency loss after 2.1 hours.

EXAMPLE 2

A composition analogous to that of Example 1 was prepared in which the PVP content was reduced to 100 mg. A solution in water (1.5 ml) showed a 10% potency loss after 1.1. hours.

EXAMPLE 3

A composition analogous to that in Example 1 but which also contained 2.5 mg of malic acid was prepared. A solution in water (1.5 ml) showed a 10% potency loss after 2.8 hours.

EXAMPLE 4

A 4 ml solution of 7.5 w/v PVP (Kollidon 12 PF) and 6.25% w/v of sodium amoxycillin was freeze dried to yield the following:
Sodium Amoxycillin: 250 mg p.f.a.
PVP (Kollidon 12 PF): 300 mg
This may be reconstituted with water (1.5 ml).

EXAMPLE 5

Spray dried sodium amoxycillin (prepared as described in W. German Offenlegungsschrift No. 2734622) was formulated in a dry mix as follows:
Sodium amoxycillin: 250 p.f.a.
PVP (Kollidon 12 PF): 600 mg
On reconstitution: water (1.5 ml) a clear solution resulted which lost 10% of potency after 3.2 hours.

EXAMPLE 6

Sodium amoxycillin (prepared by precipitation as described in British Patent No. 1241844) was formulated in a dry mix as follows:
Sodium amoxycillin: 250 mg p.f.a.
PVP (Kollidon 12 PF): 1000 mg
On reconstitution in water a solution resulted which remained clear for greater than 2 hours.

What we claim is:

1. A pharmaceutical composition for the treatment of bacterial infections, which on reconstitution with water yields an injectable solution, which composition comprises a water soluble salt of amoxycillin, and polyvinylpyrrolidine (PVP) of molecular weight 1000 to 12000, wherein the weight ratio of amoxycillin salt, taken as the free acid equivalent weight, to PVP is 1:0.25 to 1:5.

2. A composition according to claim 1, wherein the PVP has a molecular weight of 2000 to 3500.

3. A composition according to claim 1, wherein the weight ratio of the amoxycillin salt, taken as the free acid equivalent weight, to PVP is 1:0.5 to 1:3.

4. A composition according to, claim 1 wherein the amoxycillin salt is sodium amoxycillin.

5. A composition according to, claim 1 also containing a water soluble solid acidic material.

6. A composition according to claim 1, or a vial, thereof wherein the amoxycillin salt and the PVP are in the form of a solid solution.

7. A solid solution, for the treatment of bacterial infections, of a water soluble salt of amoxycillin in PVP of molecular weight 1000 to 12000, wherein the weight ratio of amoxycillin salt, taken as the free acid equivalent weight, to PVP is 1:0.25 to 1:5.

8. A solid solution according to claim 7, wherein the weight ratio of the amoxycillin salt, taken as the free acid equivalent weight, to PVP is 1:0.5 to 1:3.

9. A solid solution according to claim 7, wherein the amoxycillin salt is sodium amoxicyllin.

10. A solid solution according to, claim 7 wherein the PVP has a molecular weight of 2000 to 3500.

11. A solid solution according to, claim 7 in powder form.

* * * * *